(12) United States Patent
Cazenave et al.

(10) Patent No.: US 10,537,455 B2
(45) Date of Patent: Jan. 21, 2020

(54) GASTRIC CALIBRATION BAND

(71) Applicant: MEDICAL INNOVATION DEVELOPPEMENT, Dardilly (FR)

(72) Inventors: Ludovic Cazenave, Lyons (FR); Vincent Frering, Collonges au Mont d'Or (FR)

(73) Assignee: MEDICAL INNOVATION DEVELOPPEMENT, Dardilly (FR)

( * ) Notice: Subject to any disclaimer, the term of this patent is extended or adjusted under 35 U.S.C. 154(b) by 0 days.

(21) Appl. No.: 15/028,779

(22) PCT Filed: Oct. 14, 2014

(86) PCT No.: PCT/FR2014/052611
§ 371 (c)(1),
(2) Date: Apr. 12, 2016

(87) PCT Pub. No.: WO2015/055941
PCT Pub. Date: Apr. 23, 2015

(65) Prior Publication Data
US 2016/0270939 A1    Sep. 22, 2016

(30) Foreign Application Priority Data

Oct. 16, 2013  (FR) ..................................... 13 60058

(51) Int. Cl.
*A61F 5/00*       (2006.01)
(52) U.S. Cl.
CPC .......... *A61F 5/0066* (2013.01); *A61F 5/0063* (2013.01); *A61F 2005/002* (2013.01)

(58) Field of Classification Search
CPC .................. A61F 5/0066; A61F 5/0063; A61F 2005/002; Y10T 24/1498
See application file for complete search history.

(56) References Cited

U.S. PATENT DOCUMENTS

| 4,634,443 A | * | 1/1987 | Haber | ..................... A61F 2/004 128/DIG. 25 |
| 5,147,389 A | * | 9/1992 | Lane | ................. A61B 17/12009 623/1.24 |
| 6,003,208 A | * | 12/1999 | Christian | ............... B65D 63/00 24/16 PB |

(Continued)

FOREIGN PATENT DOCUMENTS

| EP | 0 611 561 | 8/1994 |
| EP | 2 468 218 | 6/2012 |

(Continued)

*Primary Examiner* — Kaylee R Wilson
(74) *Attorney, Agent, or Firm* — Clark & Brody

(57) ABSTRACT

The invention relates to a non-inflatable gastric band (1) including two end areas (2, 3) and an intermediate portion (4). The inner surface (I) of the band (1) is intended to contact the stomach. The end areas (2, 3) are provided with complementary closing means (5, 6) selected from notches (5) and locking loops (6) that are mutually engageable so as to ensure that the band (1) is locked in a closed position. The end area (2) has at least one notch (5) and is intended to be inserted through at least one locking loop (6) placed on the outer surface of the end area (3) up to a locked closed position, wherein at least one notch (5) is moved beyond a locking loop (6). The end area (3) also includes a guide loop (7).

19 Claims, 4 Drawing Sheets

(56) References Cited

U.S. PATENT DOCUMENTS

| | | | | |
|---|---|---|---|---|
| 6,676,674 B1 * | 1/2004 | Dudai | ............... | A61B 17/12 606/151 |
| 6,966,875 B1 * | 11/2005 | Longobardi | ............ | A61F 5/005 600/31 |
| 2005/0277963 A1 * | 12/2005 | Fields | ............. | A61B 17/12009 606/153 |

FOREIGN PATENT DOCUMENTS

| | | |
|---|---|---|
| FR | 2 799 118 | 4/2001 |
| FR | 2 896 148 | 7/2007 |
| FR | 2 981 265 | 4/2013 |
| WO | 94/27504 | 12/1994 |
| WO | 02/096326 | 12/2002 |
| WO | 2004/019671 | 3/2004 |
| WO | 2005/072195 | 8/2005 |

* cited by examiner

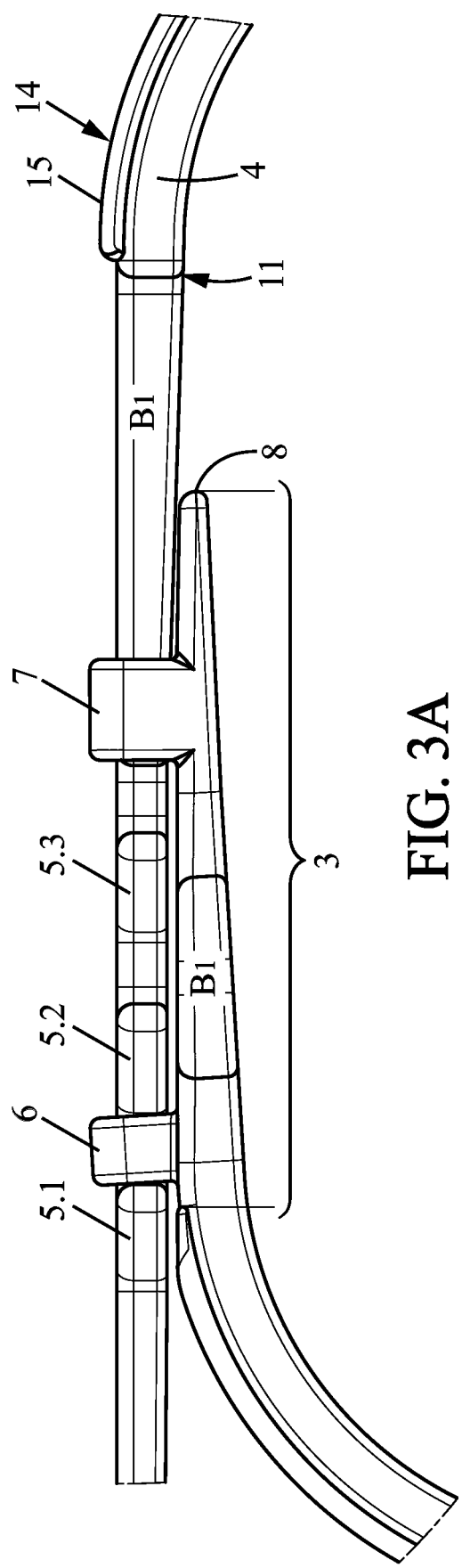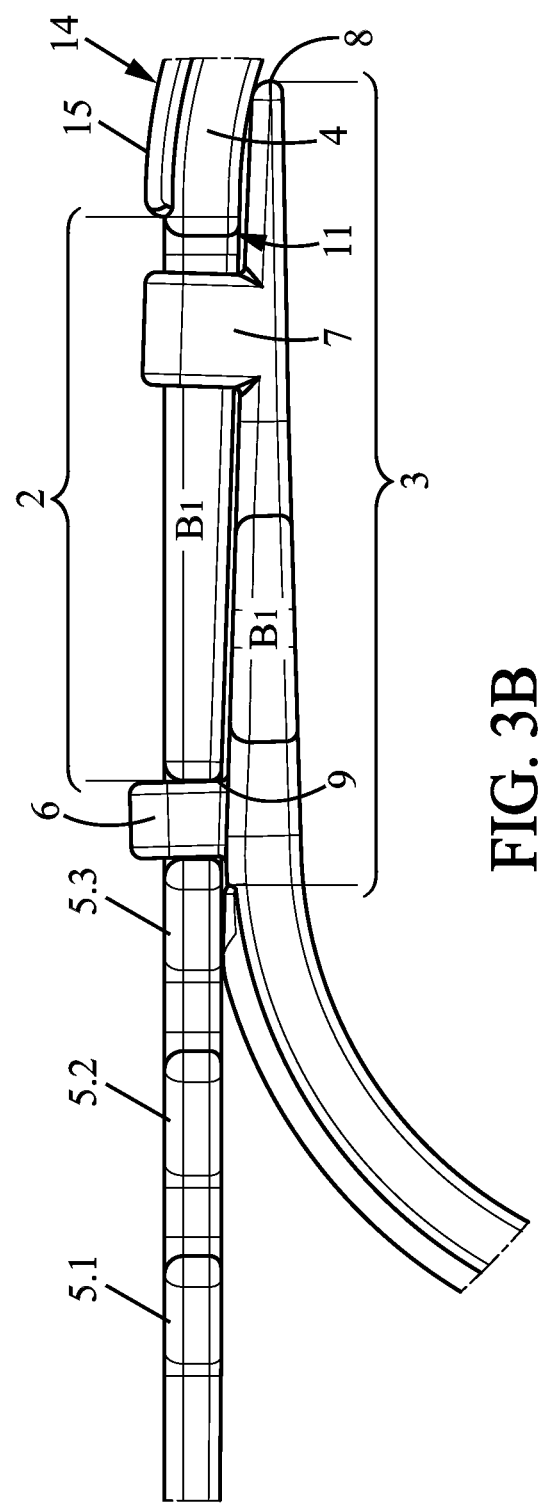

GASTRIC CALIBRATION BAND

TECHNICAL FIELD

The field of the invention is that of gastric bands which can be surgically implanted around the stomach, for the treatment of obesity by gastroplasty.

TECHNOLOGICAL BACKGROUND TO THE INVENTION

Obesity is threatening the health of an increasing number of patients. There are numerous treatments for obesity, such as diets, medical treatments and cosmetic surgery but also surgical procedures. Thus, bariatric surgery is a solution for the care of morbidly obese patients with a body mass index BMI greater than 40 or greater than 35 with a co-morbidity. Bariatric surgery consists of restricting the absorption of food, in effect reducing a patient's daily calorie intake, and thus combating obesity. It brings together a set of techniques which can be classified into two main types of intervention:
  the first aim to reduce gastric capacity, i.e. the useful volume of the stomach, and/or to reduce the emptying rate of the stomach in order to more rapidly achieve a feeling of fullness. These include gastroplasty using a variable gastric ring and vertical band gastroplasty by stapling or longitudinal sleeve gastrectomy;
  the second, so-called mixed type combine with this gastric restriction the creation of a bypass system in the digestive tract in order to reduce the absorption of nutritive elements by the intestine: gastric short-circuit or gastric by-pass.

Intervention techniques of the second type are implemented mainly after other medical therapies have failed. Longitudinal sleeve gastrectomy as well as gastric by-pass operations are very popular because they give good results in terms of weight loss. However, in recent years, patients having undergone a gastric by-pass operation some ten years previously have been found to put weight back on. This is explained by the fact that, over the course of time, the stomach becomes dilated. As the longitudinal sleeve gastrectomy operation is more recent, the scientific community still lacks the necessary retrospective view to determine the developments and consequences of this operation, but this same problem of dilation may justifiably be feared.

For these two operations the need to limit the dilation of the stomach and to calibrate the stomach therefore appears to be of the utmost importance.

It is known, for example from patent applications FR 2 799 118, FR 2 799 118, FR 2 981 265, EP 0 611 561, WO 94/27504, WO 2004/019671, to use gastric rings that can be inflated with a physiological liquid thus making it possible to restrict the stomach and thus reduce its diameter. However, suitable inflation of the ring is a delicate and relatively complex operation. Furthermore, it requires a sub-cutaneous module involving risks of leakage and contamination.

Documents WO 02/096326, FR 2 896 148 and WO 2005/072195 make it possible to overcome these drawbacks by proposing gastric rings without an inflatable portion. However, these devices also have numerous drawbacks:
  the inner diameter that they provide in the closed position cannot be adjusted, which results in significant costs because rings of different sizes have to be produced,
  they are rigid or semi-rigid in structure and are not well tolerated by the patient (inclusion phenomenon),
  they are difficult to fit around the stomach which results in risks for the patient,
  and/or they are provided with thick and/or protruding closing systems which risk injuring the area around the stomach or the stomach itself during the fitting of the ring, or once the ring has been fitted.

OBJECTIVES OF THE INVENTION

The present invention is intended to overcome at least one of the different drawbacks mentioned above, by proposing a non-inflatable gastric band that is flexible and preferably pre-formed in order to allow easier fitting.

The atraumatic aspect of such a gastric band, for the stomach and its surrounding area, is particularly desirable. Thus, it preferable for the band to be as smooth as possible on its inner surface and for roughness to be minimized, in particular regarding its closing system, in order to avoid the risks of lesions, irritation, perforations of the gastric wall or surrounding organs or the risks of inclusion requiring further surgical operations.

The present invention aims to significantly and permanently improve weight loss in patients who are overweight or morbidly obese.

The present invention also aims to provide a gastric band with an inner diameter which can be adjusted by tightening the latter around the stomach to be surrounded, to a greater or lesser degree depending on the implantation configuration and the morphology of the patient operated on. This adjustment is made only during the fitting of the band and not subsequently.

In summary, such a band has the purpose of satisfying at least one of the objectives listed below:
  i being simple to put in position and lock around the portion of stomach to be surrounded and calibrated.
  ii being comfortable and having no harmful effect on the patient's health.
  iii being biocompatible.
  iv being safe and reliable, in particular untearable.
  v offering optimum locking around the portion of the stomach to be surrounded.
  vi being able to mass-produced according to stringent quality standards and at the lowest possible cost.
  vii being at least partly radio-opaque.
  viii being easy to implant, in a manner that is stable, non-aggressive for the stomach and the surrounding organs and efficient in terms of calibration of the portion of stomach to be surrounded.

The present invention also aims to provide a method and a mould for producing the band which is viable and simple to implement on an industrial scale.

The present invention also aims to provide a simple, safe and economical method for the treatment of obesity, preferably by calibration of the stomach following an operation of the longitudinal sleeve gastrectomy type or gastrectomy of the "by-pass" type, preferably of the "by-pass" type, said method consisting of surgically implanting the gastric band referred to in the objectives above.

The present invention also aims to provide a surgically implantable gastric band, suitable for a simple, safe and economical treatment of obesity, preferably by calibration of the stomach following an operation of the longitudinal sleeve gastrectomy type or gastrectomy of the "by-pass" type, preferably of the "by-pass" type.

BRIEF DESCRIPTION OF THE INVENTION

By convention, throughout the present disclosure, any singular also denotes a plural and vice versa.

These objectives, among others, are achieved by the present invention which relates to a non-inflatable gastric band comprising two end areas and an intermediate portion with a solid cross section situated between the two end areas, the gastric band having an inner surface, on the one hand, linked to an outer surface of the gastric band by two edges, and, on the other hand, intended to come into contact with the part of the stomach encircled by the gastric band, the end areas being equipped respectively with complementary closing means capable of cooperating with each other in order to ensure locking in the closed position of the gastric band, these closing means of the gastric band being chosen from at least one notch and at least one locking loop, one of the end areas—hereafter referred to as "end area with notch(es)"—bearing at least one notch, preferably at least two, more preferentially three notches, and being intended to be inserted through at least one locking loop arranged on the outer surface of the other end area, up to a locked closed position in which at least one notch is moved beyond at least one locking loop, in which at least the end area, the outer surface of which bears at least one locking loop—hereafter referred to as "end area with loop(s)"—also comprises at least one guide loop, preferably closer to a free end of the end area with loop(s) than the locking loop, so that during the closing and locking of the gastric band, the notch or notches pass through the guide loop before passing through the locking loop or loops.

The gastric band according to the present invention is a substantially flat, long and narrow device, intended to enclose a part of the stomach. It is a calibration band which, on the one hand, gives a desired dimension to the part of the stomach arranged downstream or upstream of the calibration band and intended to receive the food bolus, and, which, on the other hand, due to the restriction that it imposes, prevents the dilation of this reduced part of the stomach which is useful to the patient for limiting the ingestion of food.

This avoids the patient having to undergo a new longitudinal sleeve gastrectomy or by-pass gastric operation with all the concomitant risks.

This band is moreover safe, reliable, atraumatic for the stomach and its environment, of a reasonable cost and capable of being produced on an industrial scale in accordance with the required quality and productivity standards.

The locking loop of the band is for example in the shape of an arch.

In the preferred embodiment of the invention, the band has a single locking loop. It is situated on the outer surface of the band and on the end area with loop(s) of the band, preferably at the end of the latter at the join between the end area bearing the locking loop and the intermediate portion of the band.

The band according to the invention also comprises at least one guide loop. It is located on the outer surface of the band. This guide loop does not have a locking function, it can facilitate the fitting of the band around the stomach and/or its stability around the stomach. When the surgeon is closing the band around the stomach, more precisely when moving the end area bearing at least one notch towards the end area bearing at least one loop, when the guide loop is located in front of the locking loop, the guide loop makes it possible to more easily insert the tongue or extension of the end area bearing at least one notch towards the locking loop which is located in the same longitudinal axis as the guide loop. Irrespective of the position of the guide loop vis-à-vis the locking loop, the guide loop makes it possible to prevent the edges of the band in the closed position from becoming displaced at an angle and no longer being parallel. It thus makes it possible to stabilize the band in the closed position around the stomach.

The guide loop is preferably in the form of an arch. When it is situated closer to the free end of the end area with loop(s) than the locking loop, it preferably has a greater, wider cross-sectional area than the cross-sectional area of the locking loop, this cross-sectional area being measured in the direction of the width of the band. When the guide loop is located further from the free end of the end area with loop(s) than the locking loop, it can have a cross-sectional area substantially identical to or greater than that of the locking loop.

In a preferred embodiment of the band, the guide loop is inserted on either side of the band over its width and forms the entire width of the band.

A minimum distance between the guide loop and the locking loop also makes it possible to ensure the stability of the band once it is closed and locked.

This distance can be comprised between 10 mm and 30 mm, preferably between 12 mm and 20 mm, for example of the order of 15 mm.

Such arrangements concerning the guide loop could be implemented in an inflatable gastric band.

The band according to the invention has a length comprised between 50 mm and 90 mm, preferably between 60 and 80 mm, for example of the order of 65 and 75 mm.

In the case of the by-pass calibration, the circumference of the band is comprised between 5 cm and 8.5 cm, more preferentially between 5.5 cm and 7.5 cm, even more preferentially between 6 and 7.5 cm.

In a manner complementary to or independent of the arrangements concerning the guide loop, in the closed position of the gastric band, the end area with notch(es) and the end area with loop(s) can overlap at least partially and the end area with loop(s) can be bevelled in its thickness, preferably in the longitudinal direction of the band.

According to such arrangements, the invention can relate to a non-inflatable gastric band comprising two end areas and an intermediate portion with a solid cross section situated between the two end areas, the gastric band having an inner surface, on the one hand, linked to an outer surface of the gastric band by two edges and, on the other hand, intended to come into contact with the part of the stomach encircled by the gastric band, the end areas being equipped respectively with complementary closing means capable of cooperating with each other in order to ensure locking in the closed position of the gastric band, these closing means of the gastric band being chosen from at least one notch and at least one locking loop, one of the end areas—hereafter referred to as "end area with notch(es)"—bearing at least one notch and being intended to be inserted through at least one locking loop arranged on the outer surface of the other end area up to a locked closed position in which at least one notch is moved beyond at least one locking loop, in which, in the closed position of the gastric band, the end area with notch(es) and the end area the outer surface of which bears at least one locking loop—hereafter referred to as "end area with loop(s)"—overlap at least partially, and in which the end area with loop(s) is bevelled in its thickness, preferably in the longitudinal direction of the gastric band.

Such arrangements concerning the bevelled end area with loop(s) could be implemented in an inflatable gastric band.

In the closed position, the two end areas of the band overlap at least partially and are fixed to each other by a "notch/loop" anti-reverse locking system. In this position, the inner surface (I) of the band is substantially circular in side view.

The at least partial overlapping of the two end areas means that the end area with notch(es) and the end area with loop(s) are at least partially superimposed in the longitudinal direction of the band. It is preferably the end area with notch(es) which at least partially covers the end area with loop(s). The superimposition is not necessarily perfect. If the overlapping is complete, then the end area with loop(s) is completely covered by the end area with notch(es) and the notches themselves.

In the closed position of the band in which its end areas overlap at least partially, the surfaces of the edges B1, B2 of the end areas of the band are preferably substantially coplanar.

According to a preferred embodiment of the invention, in a manner complementary to or independent of the arrangements concerning the guide loop, the end area with notch(es), is itself also bevelled in its thickness, preferably in the longitudinal direction of the band. Even more preferentially, the end area with notch(es) and the end area with loop(s) respectively have complementary bevels in the closed position of the gastric band.

The bevels are described as complementary because their slopes are opposite, so that when the overlapping of the two end areas is complete and the band is in closed position, locked, the thickness of the band formed by the meeting of the two end areas is substantially constant at any point of the overlapping, without taking into account the thickness of the locking loop or loops and/or of the guide loop of the band.

Preferably, the free end of the end area with loop(s) can be thinner than the remainder of the end area with loop(s). Moreover, the end area with notch(es) can have a free end thinner than the remainder of the end area with notch(es).

In an even more preferred embodiment, the thickness of the end area with notch(es) and/or of the end area with loop(s) gradually increases from the free end up to the join between said end area with notch(es) or with loop(s) and the intermediate portion of the band.

For example, the bevelled surface of the end area with loop(s) is its outer surface of the band, whereas the bevelled surface of the end area with notch(es) is its inner surface of the band, the thickness of each area increasing from its free end.

Such bevelling makes it possible, on the one hand, to minimize roughness, in particular on the inner surface of the band and, on the other hand, to have as thin a band as possible.

The end area with notch(es) can overlap at least partially the end area with loop(s) the inner surface of which forms a part of the inner surface of the band intended to be in contact with the stomach.

In a useful embodiment of the band according to the invention, the guide loop defines a passage for the notch(es), and its dimensions, on the one hand, are too great to allow a anti-reverse locking of the notch(es), and, on the other hand, are greater than those of the passage defined by the locking loop.

According to a variant, the guide loop and the locking loop could form only one single loop, with a passage with dimensions, for example of cross section, decreasing from the entry point of the guide loop to the exit point of the locking loop.

Advantageously, the notch or notches are borne by a terminal tongue extending the end area with notch(es) and are arranged substantially in the same plane as that of the end area with notch(es), the notch or notches projecting with respect to the edges of the terminal tongue. Thus, the notch or notches borne by the end area with notch(es) are wider than the width of the tongue at its terminal part.

The notch or notches have a shape that does not allow the reopening of the already closed band, so that when the notch is passed through the loop, it offers a resistance against the loop. They have an anti-reverse shape. They are preferably in the shape of fir-trees or arrows, or even dovetailed.

Each notch can have a width measured in the plane of the gastric band, the guide loop being produced in the shape of an arch having a width substantially equal to the width of each notch. The end area with notch(es) can comprise a terminal part interposed between a part comprising each notch and the intermediate portion, the terminal part having a width equal to the width of each notch.

Preferably, an angle α of the bevel between the inner surface and the outer surface of each end area with notch(es) (2) or with loop(s) (3), is comprised between 0.1° and 10°, preferably between 0.5° and 8°, and, even more preferentially between 1° and 5°.

The easy and rapid positioning of the band around the stomach to be surrounded being one of the sought advantages, the band according to the invention is preferably pre-formed, even better pre-formed as curved, for example "C"-shaped. This configuration makes it possible to facilitate the fitting of the band around the stomach for the surgeon.

Its end bearing one of more locking loops also comprises, on its outer surface, at least one guide loop which is preferably situated closer to the end of the end area than the locking loop or loops. Thus, during the closing and the locking of the band according to the invention, when the guide loop is located closer to the free end of the end area with loop(s) than the locking loop, the notch or notches borne by an end area pass through the guide loop before passing through the locking loop or loops borne by the other end area. Preferably, the guide loop has a cross-sectional area, in the width of the band, wider than the cross-sectional area of the locking loop or loops.

In the closed position, the inner surface of the band is substantially circular. It is also without folds, without invagination or hernia, and shapes itself to the remaining portion of the stomach receiving the food bolus so as to calibrate it. It has as little roughness as possible so as not to traumatize or injure the stomach by friction on the stomach wall, pinching of the latter or other means.

In a preferred embodiment, it is completely smooth, except at the area of the meeting between the end of the end area bearing at least one locking loop and the inner surface of the band at the join between the end area bearing the notches and the intermediate portion of the band. In fact, as the thickness of the bevel of the end of the end area bearing at least one loop is minimal but cannot necessarily be absolutely zero, at the level of this abovementioned meeting, there is a slight thickness which means that the inner surface of the band in the closed position is not completely smooth but there is a slight discontinuity at this level.

Preferably, at least one of the longitudinal edges of the band is blunt or rounded so as not to have projecting angles capable of injuring the patient.

This band according to the invention is made of a flexible or semi-rigid material of hardness D1 and is chosen from the group of the biocompatible flexible elastomers, comprising, or even better constituted by, silicone or analogous elastomers. According to a preferred feature of the invention, the hardness D1 of the band is comprised between 30 and 80 Shore A, preferably 50 and 70 Shore A, for example of the order of 60 Shore A.

Because of this precise implantation of the band on the stomach, the dimensions of the band according to the invention can be significant. The band is therefore preferably narrow, preferably with a maximum width of approximately 1 cm±20%.

The length of the band between its two end areas can also be significant as it determines the calibration of the stomach pouch receiving the food bolus. The band must be in contact with the stomach pouch receiving the food bolus, otherwise it is not held in place as it is preferably not fixed. Thus, the band must not be too long. Its length must be comprised between 50 mm and 90 mm, preferably between 60 and 80 mm.

The thickness of the band varies over its length. The band according to the invention has a thickness comprised between 0.8 mm and 2 mm.

It is particularly useful that the band according to the invention comprises at least one radio-opaque part (for example a radio-opaque insert), preferably borne by the outer surface (E). This makes it possible for it to be detected by different radiation, in particular by X-rays. This insert makes the band slightly thicker.

Preferably, the longitudinal edges of the outer surface are protruding, and, even more preferentially, are at least partly radio-opaque, in particular to X-rays.

In order to facilitate the work of the surgeon, the band according to the invention can comprise at least one, preferably at least two projections for endoscopic handling, preferably located at the end area with loop(s), and even more preferentially, each of the two projections extending from one edge (B1,B2) of the band, preferably in the plane of the band.

These projections can adopt all possible shapes suitable for manipulation during laparoscopy. Preferably, they are rounded and in the form of lugs with edges not risking injury to the stomach or its surrounding area.

The band according to the invention can also be characterized by manufacturing features. Thus, it can be advantageously obtained by moulding using a mould. The latter has features which make it possible to indirectly define the band according to the invention. Preferably, it is moulded in a single piece.

The present invention also covers a method for producing the abovementioned band which essentially consists of moulding, preferably in a single piece, as well as a mould capable of being utilized in this method.

Another subject of the invention is a simple, safe and economical method for the treatment of obesity, preferably by calibration of the stomach following an operation of the longitudinal sleeve gastrectomy type or gastrectomy of the "by-pass" type, preferably of the "by-pass" type, said method consisting of surgically implanting the abovementioned gastric band.

More precisely, a band as defined in the present disclosure is put in position and locked around a patient's remaining portion of stomach receiving the food bolus, in order to reduce or avoid the dilation of the remaining portion of stomach.

In practice, after a longitudinal sleeve gastrectomy or a by-pass gastrectomy, the surgeon puts the open band according to the invention in place around the portion of stomach which will receive the food bolus or the proximal stomach pouch, just below the oesophagus. He closes this band by securing its ends to each other. Preferably, once the band is locked in the closed position around the stomach, the extension portion bearing the notches remaining beyond the locking loop is cut so as not to injure the stomach or the surrounding area of the latter, it being understood that the cutting is done beyond the notch so as not to compromise the locking of the band. The proximal stomach pouch is then gripped by the band thus preventing its dilation. This operation is delicate and requires precision as the band must be fitted so as not to compromise the vascularization of the stomach.

Preferably, the band according to the invention is not fixed on the stomach.

Another subject of the invention is a surgically implantable gastric band, suitable for a simple, safe and economical treatment of obesity, preferably by calibration of the stomach following an operation of the longitudinal sleeve gastrectomy type or gastrectomy of the "by-pass" type, preferably of the "by-pass" type.

DESCRIPTION OF A PREFERRED EMBODIMENT OF THE INVENTION

Other notable features will become apparent from the following description of a preferred embodiment of the band according to the invention.

This detailed description is given with reference to the attached figures in which:

FIG. 3A is a detailed view of the band of FIG. 3.

FIG. 3B is a variant of FIG. 3 closed/locked at the maximum level of the third notch.

Figure 1:
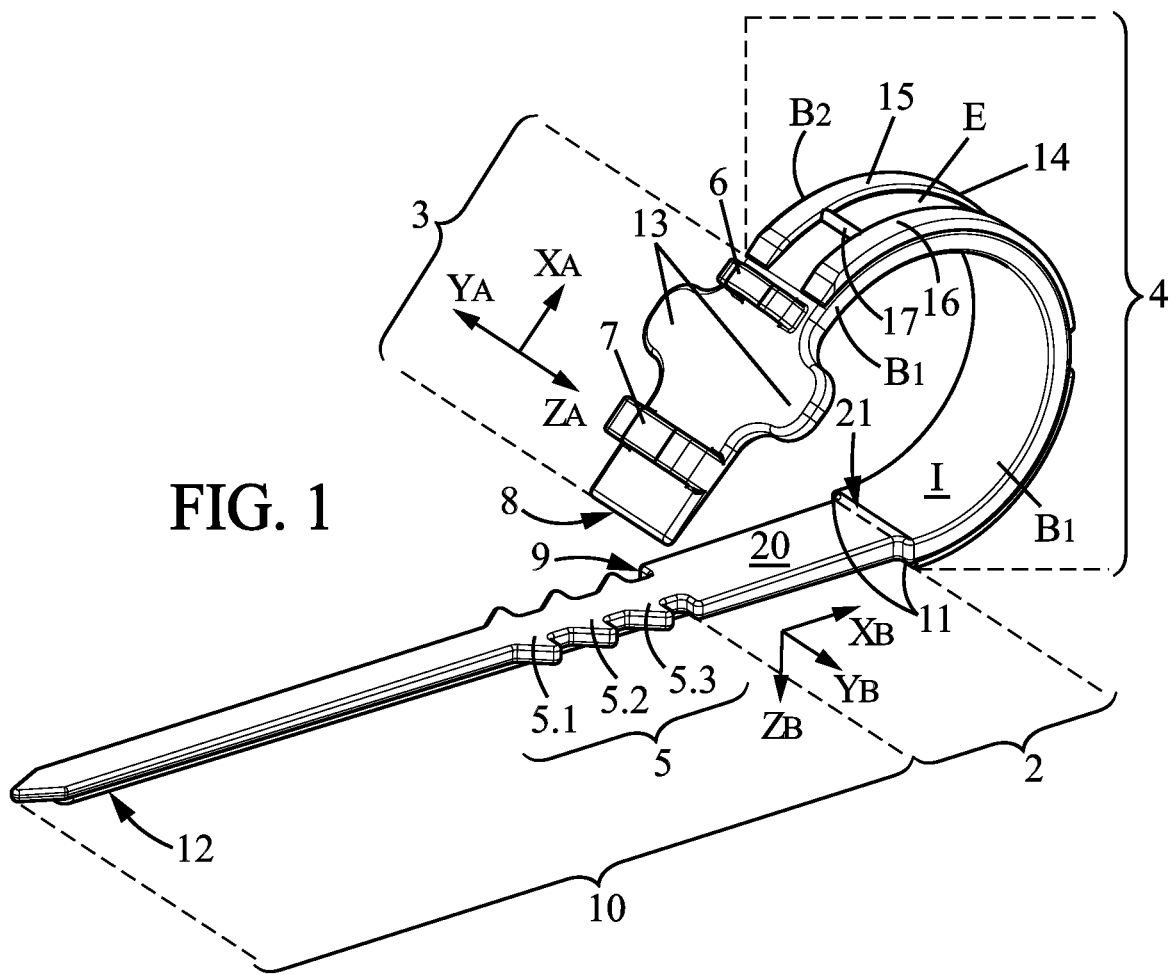
FIG. 1 represents a perspective view of the band according to the invention, not closed.

As shown in the attached figures, the band (1) according to the invention is a gastric band intended to encircle and calibrate a part of the stomach with which it comes into contact via its inner surface (I).

This flexible, non-inflatable band (1), e.g. produced by moulding an elastomer such as a silicone elastomer, has an inner surface (I) intended to come into contact with the stomach and linked by two edges (B1,B2) to an outer surface (E). It comprises:

- a so-called end area "with notches" (2), the free end (9) of which has an extension formed by a tongue (10) having three notches (5), respectively (5.3-5.2-5.1) from the base towards the end of the tongue (10);
- an end area (3) provided with a locking loop (6) and a guide loop (7) which extend in a direction substantially perpendicular to the outer surface of this so-called end area "with loops" (3);
- an intermediate portion (4) situated between the two end areas (2) and (3) which are two extensions of this intermediate portion (4); the outer surface (E) of this intermediate portion (4) being covered with a radio-opaque insert (14).

The two end areas (2) and (3), the tongue (10) and the intermediate portion (4) have a solid cross section. The three notches (5) and the loops (6, 7) of this band (1) of substantially rectangular, straight cross section, are complementary closing means (5, 6) capable of cooperating with each other to ensure the closing and locking in the closed position of the band (1) formed by bringing the two end areas (2) and (3) towards each other.

The three notches (5.1-5.2-5.3) are triangular extensions of the edges of the tongue (10) in the plane of the latter, parallel to or in the plane ($x_B;y_B$) defined by the three-dimensional frame of reference ($x_B;y_B;z_B$) of FIG. 1. These three notches (5.1-5.2-5.3) are, in this embodiment example, of identical shapes and dimensions. But it could be otherwise.

The end area (2) with notches (5) is divided into two parts: a terminal part (20) delimited by the free end (9) and by a shoulder (11) and a linking part (21) extending between the shoulder (11) and the join between the end area (2) with notches and the intermediate portion (4).

An extra thickness (12) for reinforcement extends from the terminal part (20) of the end area (2) with notches, over the outer surface of the tongue (10).

On the outer surface of the end area (3) with loops, the guide loop (7) is closer to the free end (8) of the end area (3), than the locking loop (6). The locking loop (6) is situated in the vicinity of the top of the slope of the bevel of the end area (3) with loops, this top being itself substantially at the join between the end area (3) with loops and the intermediate portion (4).

Moreover, the cross-sectional area of the guide loop (7) of the band (1) is greater than that of the locking loop (6). The same applies to the widths of these loops along the axis ($y_A$) defined by the three-dimensional frame of reference ($x_A;y_A;z_A$) of FIG. 1.

Figure 6:
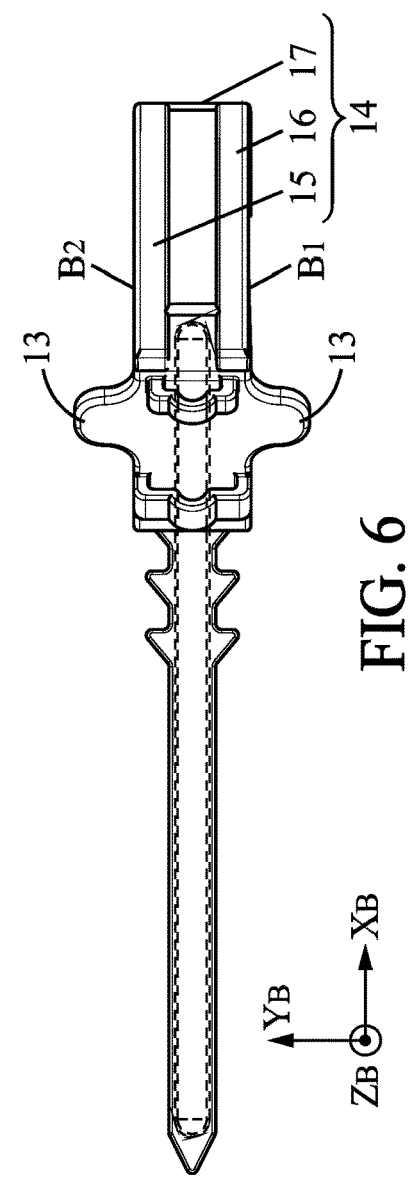
FIG. 6 is a top view of a variant of FIG. 2.

As shown by FIGS. 1 and 6, the band (1) has two projections (13)—or lobes—for endoscopic handling, each extending from an edge (B1, B2) of the end area (3) with loops. These lobes 13 are situated in the plane ($x_A,y_A$) of the width of the band (1).

In this preferred embodiment of the band (1) according to the invention, the two end areas (2) and (3) of the band are bevelled in their thickness, along the longitudinal direction given by the axis ($x_B$),($x_A$), so that this thickness gradually decreases from the join between the end area (2),(3) and the intermediate portion (4) towards the free end (8),(9).

Figure 4:
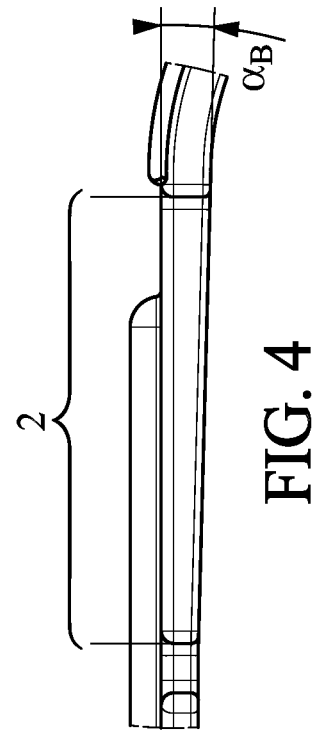
FIG. 4 is a detail of FIG. 2 (circle V of FIG. 2) showing in side view the bevelled end area with notches.

The bevel of the end area (2) with notches can be defined by the angle $\alpha_B$ between its inner surface and its outer surface which is only an extension of the outer surface (E) of the band (1) in the closed and locked position of the latter. The angle $\alpha_B$ which appears in FIG. 4 is comprised between 1 and 5°, for example 4° in this case.

Figure 5:
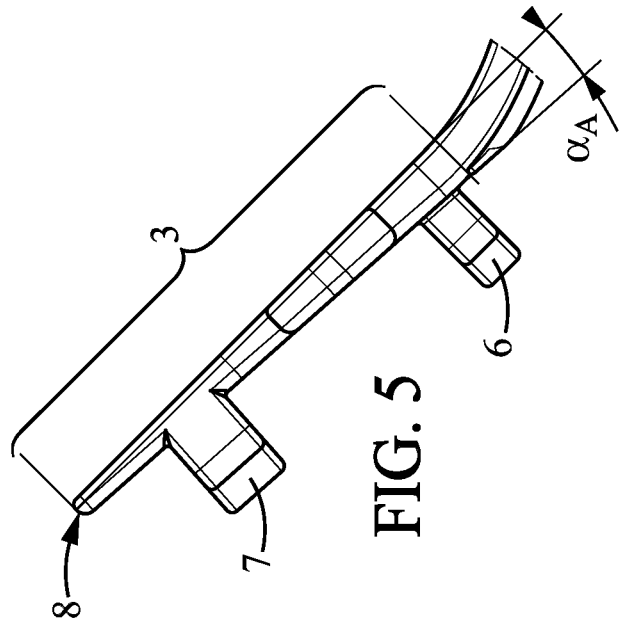
FIG. 5 is a detail of FIG. 3 (circle IV of FIG. 3) showing in side view the bevelled bearing end area with loop(s).

The bevel of the end area (3) with loops can be defined by the angle $\alpha_A$ between its outer surface bearing the loops (6, 7) and its inner surface which is an integral part of the inner surface (I) of the band (1) in the closed and locked position of the latter. The angle $\alpha_A$ which appears in FIG. 5 is comprised between 1 and 5°, for example 4° in this case.

Preferably, $\alpha_B=\alpha_A$ for the overlapping to be complementary. These bevels serve to improve and facilitate the closing of the band around the stomach.

In FIG. 1, the radio-opaque insert (14) is formed by two parallel borders (15, 16), proud of the surface (E) and linked by 3 c (17). It is constituted for example by a elastomer of the same type or not of the same type as the band (1).

Figure 2:
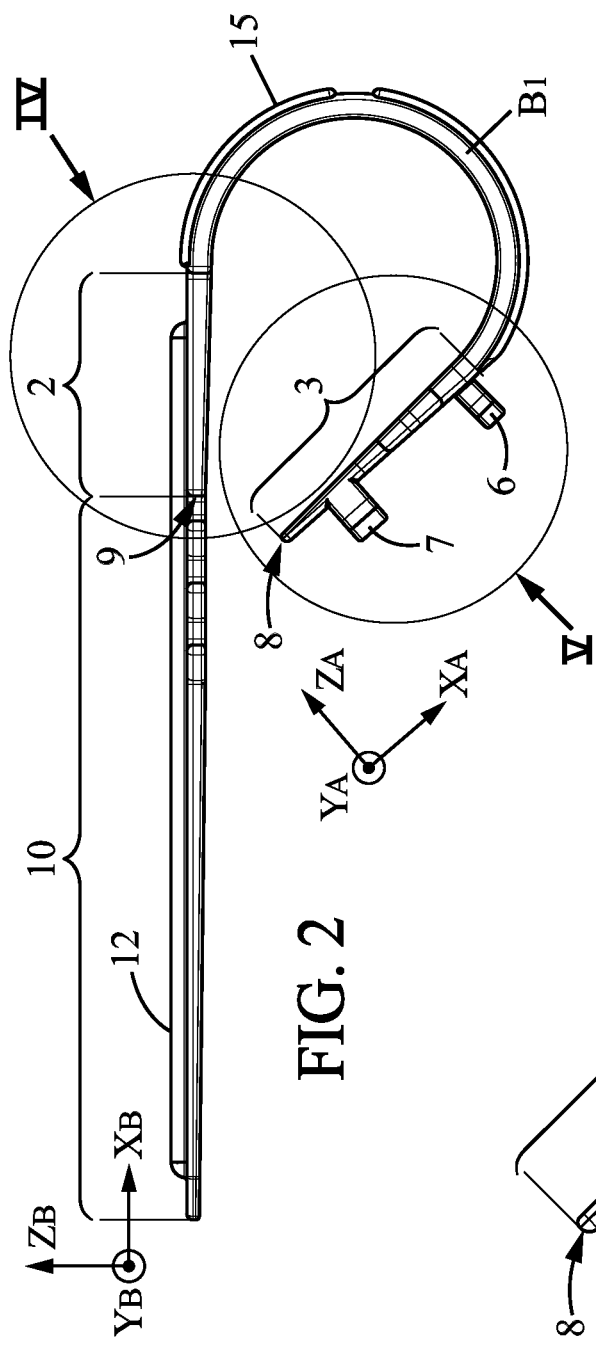
FIGS. 2 and 3 represent side views of the band according to the invention, in the open and closed/locked positions respectively at the level of the first notch.

As shown in FIGS. 1 and 2, the band is pre-formed so that when disengaged, i.e. not closed/locked, it is essentially curved in its intermediate portion (4)—for example over an angular sector comprised between 150 and 270°-225° in this case—whereas the end area (3) with loops, the end area (2) with notches and its notched tongue extending the latter, are substantially straight.

This curved pre-form makes it possible to facilitate the closing of the band around the stomach, in particular by limiting the surgeon's movements. Furthermore, the end area (3) bearing at least one loop (6) is straight and the cross-sectional areas of the guide loop (7) and of the locking loop (6) are aligned along the same axis, the longitudinal axis $x_A$ of the band. The tongue or extension bearing at least one notch is passed through the guide loop and the locking loop in a single movement by the surgeon, thus limiting the latter's movements and the operating time.

FIGS. 3A and 3B show respectively a locking with the notch (5.1)—closest to the end of the tongue (10)—and with the third notch (5.3)—closest to the free end (9) of the area (2) with notches.

In the position of FIG. 3B, the third notch (5.3) is passed through the locking loop (6) and its base is supported on the surface of the loop (6) turned towards the intermediate portion (4) and the free end (9) butts up against the face of the loop (6) turned towards the guide loop (7).

Moreover, the shoulder (11) between the parts (20) and (21) of the area (2) with notches, butts up against the face of the guide loop (7) turned towards the free end (8) of the area (3) with loops.

Thus, the band can be closed/locked in a simple, safe, stable and atraumatic manner, around the stomach. In fact, angular displacements of the end area bearing at least one notch relative to the end area bearing at least one loop are then impossible. These two end areas remain correctly overlapping and their respective edges remain perfectly parallel.

Figure 3:
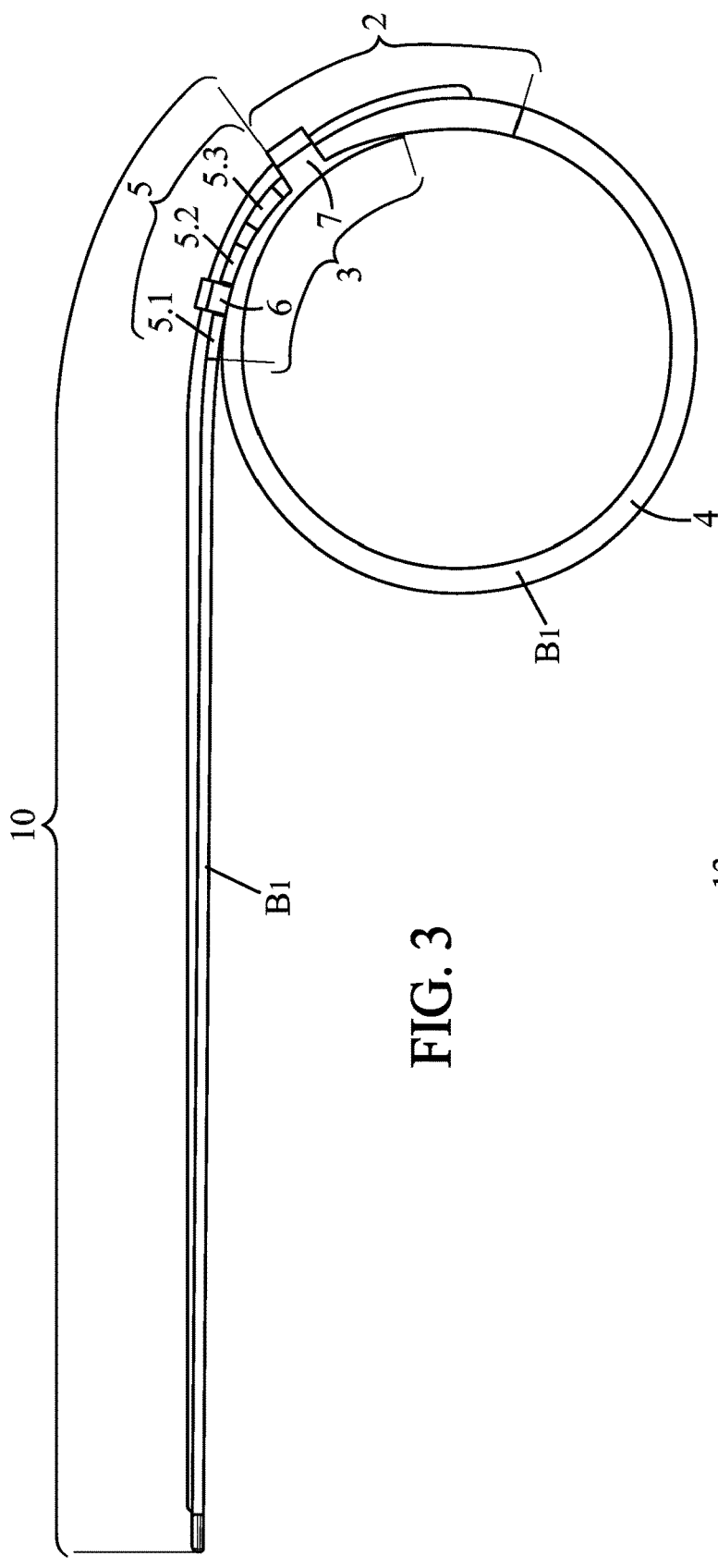

As shown in FIG. 3, the band in the closed and locked position is substantially circular in side view.

FIGS. 3, 3A and 3B show that the bevels of the respective end areas (2) and (3) have inverse slopes. The end area (2) with notches therefore overlaps the end area (3) with loops in a complementary manner.

The overlapping is greater in the locking with the notch 5.3 of FIG. 3B. This overlapping of the bevels tends to minimize the thickness (axes $z_A;z_B$ in FIG. 1) in this area and limits, or even eliminates, the roughness that can be formed by the free end (8) on the inner surface (I) of the band intended to be in contact with the stomach.

The edges of the band (1) according to the invention are advantageously blunt so as not to injure the patient.

It is provided according to a notable feature of the invention, that the band is in a single piece and is produced from at least one silicone elastomer with a hardness comprised for example between 30 and 80 Shore A, preferably 50-70 Shore A, for example of the order of 60 Shore A.

The band (1) according to the invention can be put in position by conventional surgery or by laparoscopy, around the stomach and more precisely around the portion of the stomach receiving the food bolus, within the context of a "by-pass" operation, around the proximal stomach pouch. The C-shaped preform and the straight shape of the end areas and of the tongue with notches, as well as the lobes for endoscopic handling (13) are all assets facilitating manipulation of this band (1) by the surgeon.

This band (1) does not require fixing to the stomach, which is another decisive advantage, so as not to add work to the surgery.

The invention claimed is:

1. Non-inflatable gastric band made in one piece of molded elastomer, the gastric band comprising an end area with notch(es), an end area with loop(s), and an intermediate portion with a solid cross section situated between the two end areas, the gastric band having an inner surface-linked to an outer surface of the gastric band by two edges and wherein the inner surface is intended to come into contact with a part of a stomach encircled by the gastric band, the two end areas being equipped respectively with complementary closing means capable of cooperating with each other in order to ensure a locking in a closed position of the gastric band, the closing means of the gastric band including at least one notch on the end area with notch(es) and at least one locking loop on an outer surface of the end area with loop(s), the at least one locking loop being integral with the end area with loop(s), wherein the end area with notch(es) is intended to be inserted through the at least one locking loop arranged on the end area with loop(s) up to the locked closed position in which the at least one notch is moved beyond the at least one locking loop, the end area with notch(es) including a terminal tongue arranged substantially in a plane of the gastric band between parallel longitudinal edges, and at least two adjacent enlarged portions projecting with respect to the longitudinal edges of the terminal tongue, each of the adjacent enlarged portions having a width measured in a plane of the gastric band, the at least one notch being formed between the at least two adjacent enlarged portions, wherein the end area with the loop(s) also comprises at least one guide loop arranged on the outer surface of the end area with loops(s) and integral with the end area with loop(s), the at least one guide loop defining a passage for the at least one notch, the at least one guide loop forming of an arch having dimensions that are too large to allow an anti-reverse locking of the at least one notch, and greater than dimensions of a passage defined by the at least one locking loop, the at least one guide loop having a width equal to the width of the at least two adjacent enlarged portions, the at least one guide loop being closer to a free end of the end area with loop(s) than the at least one locking loop, so that during closing and locking of the gastric band, the at least one notch passes through the at least one guide loop before passing through the at least one locking loop.

2. Gastric band according to claim 1 in which, in the closed position of the gastric band, the end area with notch(es) and the end area with loop(s) overlap at least partially, and in which the end area with loop(s) is bevelled in thickness.

3. Gastric band according to claim 2, in which the free end of the end area with loop(s) is thinner than a remainder of the end area with loop(s).

4. Gastric band according to claim 2, in which the end area with notch(es) is bevelled in thickness.

5. Gastric band according to claim 4, in which the end area with notch(es) and the end area with loop(s) are bevelled in a complementary manner in the closed position of the gastric band.

6. Gastric band according to claim 4, in which the end area with notch(es) has a free end thinner than a remainder of the end area with notch(es).

7. Gastric band according to claim 4, in which a thickness of the end area with notch(es) is bevelled in a longitudinal direction of the band.

8. Gastric band according to claim 2 in which, in the closed position of the gastric band, the end area with notch(es) at least partially overlaps the end area with loop(s), an inner surface of the end area with loop(s) forming a part of the inner surface of the band intended to be in contact with the stomach.

9. Gastric band according to claim 2, in which an angle $\alpha$ of a bevel between an inner surface and an outer surface of the bevelled end area is comprised between 0.1° and 10°.

10. Gastric band according to claim 2, in which a thickness of the end area with loop(s) is bevelled in a longitudinal direction of the gastric band.

11. Gastric band according to claim 2, in which an angle $\alpha$ of the bevel between an inner surface and an outer surface of the bevelled end area is comprised between 0.5° and 8°.

12. Gastric band according to claim 2, in which an angle $\alpha$ of the bevel between an inner surface and an outer surface of the bevelled end area is comprised between 1° and 5°.

13. Gastric band according to claim 1, in which the end area with notch(es) comprises a terminal part interposed between a part comprising the at least one notch and the intermediate portion, the terminal part having a width equal to the width of the at least one notch.

14. Gastric band according to claim 1, comprising at least one radio-opaque part.

15. Gastric band according to claim 14, wherein the at least one radio-opaque part is borne by the outer surface of the gastric band.

16. Gastric band according to claim 1, comprising at least one projection for endoscopic handling.

17. Gastric band according to claim 16, wherein the at least one projection for endoscopic handling comprises at least two projections for endoscopic handling.

18. Gastric band according to claim 17, wherein each of the two projections extends from one of the edges of the gastric band.

19. Gastric band according to claim 16, wherein the at least one projection for endoscopic handling is located at the end area with loop(s).

* * * * *